United States Patent
Manzella, Jr. et al.

(10) Patent No.: US 10,010,886 B2
(45) Date of Patent: Jul. 3, 2018

(54) SPRING-OPEN SHEETING FOR FLUID PROCESSING CASSETTE

(71) Applicant: Fenwal, Inc., Lake Zurich, IL (US)

(72) Inventors: Salvatore Manzella, Jr., Barrington, IL (US); Gregory G. Pieper, Waukegan, IL (US); Terry Chung, Kildeer, IL (US); Benjamin Rockwell, Buffalo Grove, IL (US)

(73) Assignee: FENWAL, INC., Lake Zurich, IL (US)

( * ) Notice: Subject to any disclaimer, the term of this patent is extended or adjusted under 35 U.S.C. 154(b) by 339 days.

(21) Appl. No.: 14/420,686

(22) PCT Filed: Mar. 11, 2013

(86) PCT No.: PCT/US2013/030130
§ 371 (c)(1),
(2) Date: May 15, 2015

(87) PCT Pub. No.: WO2014/035471
PCT Pub. Date: Mar. 6, 2014

(65) Prior Publication Data
US 2015/0273471 A1    Oct. 1, 2015

Related U.S. Application Data

(60) Provisional application No. 61/693,804, filed on Aug. 28, 2012.

(51) Int. Cl.
*A61J 1/06* (2006.01)
*B01L 3/00* (2006.01)
(Continued)

(52) U.S. Cl.
CPC .............. *B01L 3/567* (2013.01); *A61M 1/14* (2013.01); *A61M 1/34* (2013.01); *A61M 1/36* (2013.01);
(Continued)

(58) Field of Classification Search
USPC .................. 422/501–505, 527, 533, 554, 44; 436/177, 180
See application file for complete search history.

(56) References Cited

U.S. PATENT DOCUMENTS 5,381,510 A    1/1995   Ford et al.
5,462,416 A   10/1995   Dennehey et al.
(Continued)

FOREIGN PATENT DOCUMENTS

CN    1321222 A    11/2001
CN    1658916 A     8/2005
(Continued)

OTHER PUBLICATIONS

International Search Report and Written Opinion for PCT Patent Appl'n. No. PCT/US2013/030130, dated Jun. 6, 2013.

*Primary Examiner* — Dean Kwak
(74) *Attorney, Agent, or Firm* — Cook Alex Ltd.

(57) ABSTRACT

A sheeting is provided for use with a fluid processing cassette having a valve station with a plurality of fluid flow ports. The sheeting has a generally flexible layer and a biasing member associated with the layer. The sheeting is attached to the cassette such that the biasing member is received within the valve station. The cassette may be used with a fluid processing system having a valve actuator with a piston that is aligned with the cassette during use. In an extended position, the piston presses the sheeting against the port to prevent fluid flow through the valve station. When the piston moves from the extended position to a retracted position, it allows the sheeting to uncover the port, thereby allowing fluid flow through the valve station. The biasing member assists in displacing the sheeting from the port when the piston moves to the retracted position.

16 Claims, 5 Drawing Sheets

(51) Int. Cl.
*A61M 1/14* (2006.01)
*A61M 1/34* (2006.01)
*A61M 1/36* (2006.01)

(52) U.S. Cl.
CPC ........ *B01L 3/502* (2013.01); *A61M 2205/128* (2013.01); *A61M 2205/3331* (2013.01); *B01L 2200/0689* (2013.01); *B01L 2300/049* (2013.01); *B01L 2300/123* (2013.01); *B01L 2400/06* (2013.01)

(56) References Cited

U.S. PATENT DOCUMENTS

| | | | |
|---|---|---|---|
| 5,609,572 A | 3/1997 | Lang | |
| 5,812,168 A * | 9/1998 | Pawlowski, Jr. | B41J 2/175 347/85 |
| 5,837,905 A | 11/1998 | Strauss et al. | |
| 5,868,696 A * | 2/1999 | Giesler | A61M 1/3696 494/62 |
| 8,096,422 B2 * | 1/2012 | Dorian | A61M 1/3633 210/360.1 |
| 8,961,902 B2 * | 2/2015 | Falb | B01L 3/5025 422/501 |
| 2001/0020971 A1 * | 9/2001 | Usui | B41J 2/17513 347/86 |
| 2002/0109760 A1 * | 8/2002 | Miyazawa | B41J 2/17503 347/86 |
| 2002/0159900 A1 | 10/2002 | Lawless et al. | |
| 2004/0019313 A1 * | 1/2004 | Childers | A61M 1/1696 604/5.01 |
| 2005/0134661 A1 * | 6/2005 | Miyazawa | B41J 2/17503 347/86 |
| 2011/0181004 A1 | 7/2011 | Manzella, Jr. et al. | |
| 2011/0282276 A1 | 11/2011 | Abal | |
| 2014/0109885 A1 * | 4/2014 | Kalayci | F01M 13/0011 123/572 |

FOREIGN PATENT DOCUMENTS

| | | |
|---|---|---|
| CN | 101986776 A | 3/2011 |
| CN | 102458505 A | 5/2012 |
| DE | 10 2009 024469 A1 | 1/2011 |
| EP | 1 504 777 A1 | 2/2005 |
| EP | 1 820 480 A1 | 8/2007 |
| JP | 2011-224394 A | 11/2011 |

\* cited by examiner

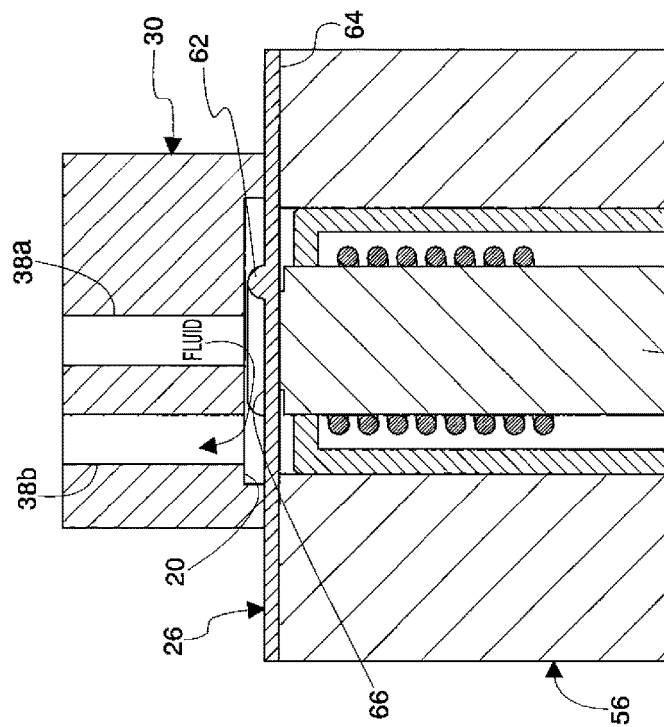
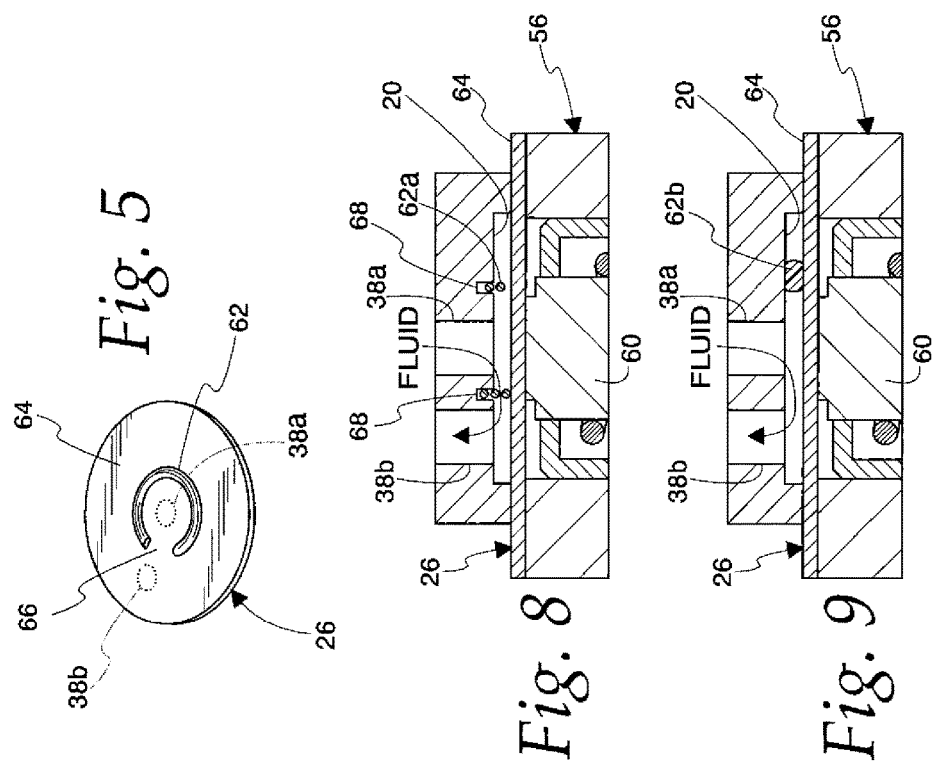

SPRING-OPEN SHEETING FOR FLUID PROCESSING CASSETTE

RELATED APPLICATION

This application is a U.S. national stage application of PCT Patent Application Ser. No. PCT/US2013/030130, filed Mar. 11, 2013, which claims the benefit of and priority of U.S. Provisional Patent Application Ser. No. 61/693,804, filed Aug. 28, 2012, the contents of which are incorporated by reference herein.

DESCRIPTION

Technical Field

The present subject matter relates to fluid processing cassettes and, more particularly, to a flexible sheeting or diaphragm of such a cassette.

Background

Whole blood is routinely separated into its various components, such as red blood cells, platelets, and plasma. Conventional blood separation methods use durable centrifuge equipment in association with single use, sterile processing sets, typically made of plastic. The configuration of the single use processing sets used in combination with different centrifuges varies widely, but some sets include a molded plastic flow control member commonly referred to as a cassette. As used herein, the term "cassette" refers to a component of a fluid processing system that includes a number of defined fluid passageways and valve stations. In addition to blood separation systems, cassettes may be employed in other fluid processing systems, such as dialysis systems, intravenous administration systems, and others.

The cassette is secured to a cassette holder of the durable equipment of the fluid processing system. The cassette holder includes actuators for opening and closing the valve stations, which determine which of the fluid passageways are connected to each other, thereby directing fluid between a number of sources and destinations.

An exemplary cassette and cassette holder are employed by the AMICUS® system marketed by Fenwal, Inc. of Lake Zurich, Ill., which is an affiliate of Fresenius Kabi AG of Bad Homburg, Germany. One version of the AMICUS® system is described in greater detail in U.S. Pat. No. 5,868,696, which is hereby incorporated herein by reference. In the AMICUS® system, fluid flow is controlled by one or more disposable cassettes with preformed fluid passages, which interface with an array of actuators and sensors located on a panel of the durable reusable hardware. Each cassette has a flexible diaphragm or sheeting on the side facing the actuators and sensors. A solenoid clamp of the hardware presses the sheeting against the cassette to cover selected fluid passages or valve stations, thereby preventing fluid flow therethrough. When it becomes desirable for fluid to flow through the fluid passages, a vacuum is applied by the hardware to assist in drawing the sheeting away from the fluid passages, thereby opening them for fluid flow therethrough. Operating the vacuum requires additional power and involves a number of mechanical parts, so for purposes of simplifying the system and reducing its power consumption, it would be advantageous to provide a system in which fluid flow through the cassette may be controlled without the need for an applied vacuum to unseat the sheeting from the fluid passages.

SUMMARY

There are several aspects of the present subject matter, which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid processing cassette includes an interior wall defining a topside and an underside, with at least one valve station associated with the underside. First and second fluid flow ports are associated with one of the valve stations. Each fluid flow port comprises a through hole in the interior wall, with the associated valve station comprising an upstanding edge surrounding the first and second fluid flow ports. The cassette further includes a sheeting overlying the underside of the interior wall, sealed or seated to the upstanding edge of each valve station, and comprising a generally flexible layer. The generally flexible layer has first and second sides, with a biasing member associated with one of the sides. The generally flexible layer further includes an intermediate region overlaying a valve station and configured so that, upon localized application of a closing force upon the intermediate region, the generally flexible layer flexes into the valve station and into contact with the underside of the interior wall within the valve station to seat against the first fluid flow port to seal the first fluid flow port, which closes the valve station for fluid flow. The biasing member is positioned between the underside of the interior wall and the generally flexible layer, within the valve station. The biasing member is biased to unseat the generally flexible layer from the first fluid flow port by directly contacting the underside of the interior wall within the valve station.

In another aspect, a fluid processing system and a disposable processi ng set are provided in combination. The combination includes a fluid processing cassette and a valve actuator. The fluid processing cassette includes an interior wall defining a topside and an underside, with at least one valve station associated with the underside. First and second fluid flow ports are associated with one of the valve stations. Each fluid flow port comprises a through hole in the interior wall, with the associated valve station comprising an upstanding edge surrounding the first and second fluid flow ports. The cassette further includes a sheeting overlying the underside of the interior wall, sealed or seated to the upstanding edge of each valve station, and comprising a generally flexible layer. The generally flexible layer has first and second sides, with a biasing member associated with one of the sides. The generally flexible layer further includes an intermediate region overlaying a valve station and movable into contact with the underside of the interior wall within the valve station to seat against the first fluid flow port to seal the first fluid flow port. The biasing member is positioned between the underside of the interior wall and the generally flexible layer, within the valve station. The biasing member is biased to unseat the generally flexible layer from the first fluid flow port by directly contacting the underside of the interior wall within the valve station. The valve actuator is configured to engage the sheeting of the cassette and includes a piston substantially aligned with the first fluid flow port when the sheeting of the cassette is in engagement with the valve actuator. The piston is configured to move been an extended position and a retracted position. In the extended position, the piston applies localized application of a closing force upon the intermediate region to flex the sheeting into the valve station and into contact with the interior wall of the cassette within the valve station so as to cover the first fluid flow port and thereby prevent fluid flow through the valve station. In the retracted position, the piston is spaced away from the cassette so as to allow the sheeting to uncover the first fluid flow port and thereby allow fluid flow through the valve station. The biasing member is configured to assist in displacing the sheeting from the first fluid flow port when the piston moves from the extended position to the retracted position.

BRIEF DESCRIPTION OF THE DRAWINGS

FIG. 5 is a detail view of a biasing member of the cassette sheeting of FIG. 3, with the relative position of the associated fluid flow ports shown in broken lines;

FIG. 6 is a cross-sectional view of a valve station of the cassette of FIG. 3 secured by the cassette holder of FIG. 2, with a piston of the cassette holder in a retracted position;

FIG. 8 is a cross-sectional view of a cassette having an alternative biasing member, secured by the cassette holder of FIG. 2; and FIG. 9 is a cross-sectional view of another cassette having an alternative biasing member, secured by the cassette holder of FIG. 2.

DETAILED DESCRIPTION OF THE ILLUSTRATED EMBODIMENTS

The embodiments disclosed herein are for the purpose of providing the required description of the present subject matter. They are only exemplary, and may be embodied in various forms. Therefore, specific details disclosed herein are not to be interpreted as limiting the subject matter as defined in the accompanying claims.

Figure 1:
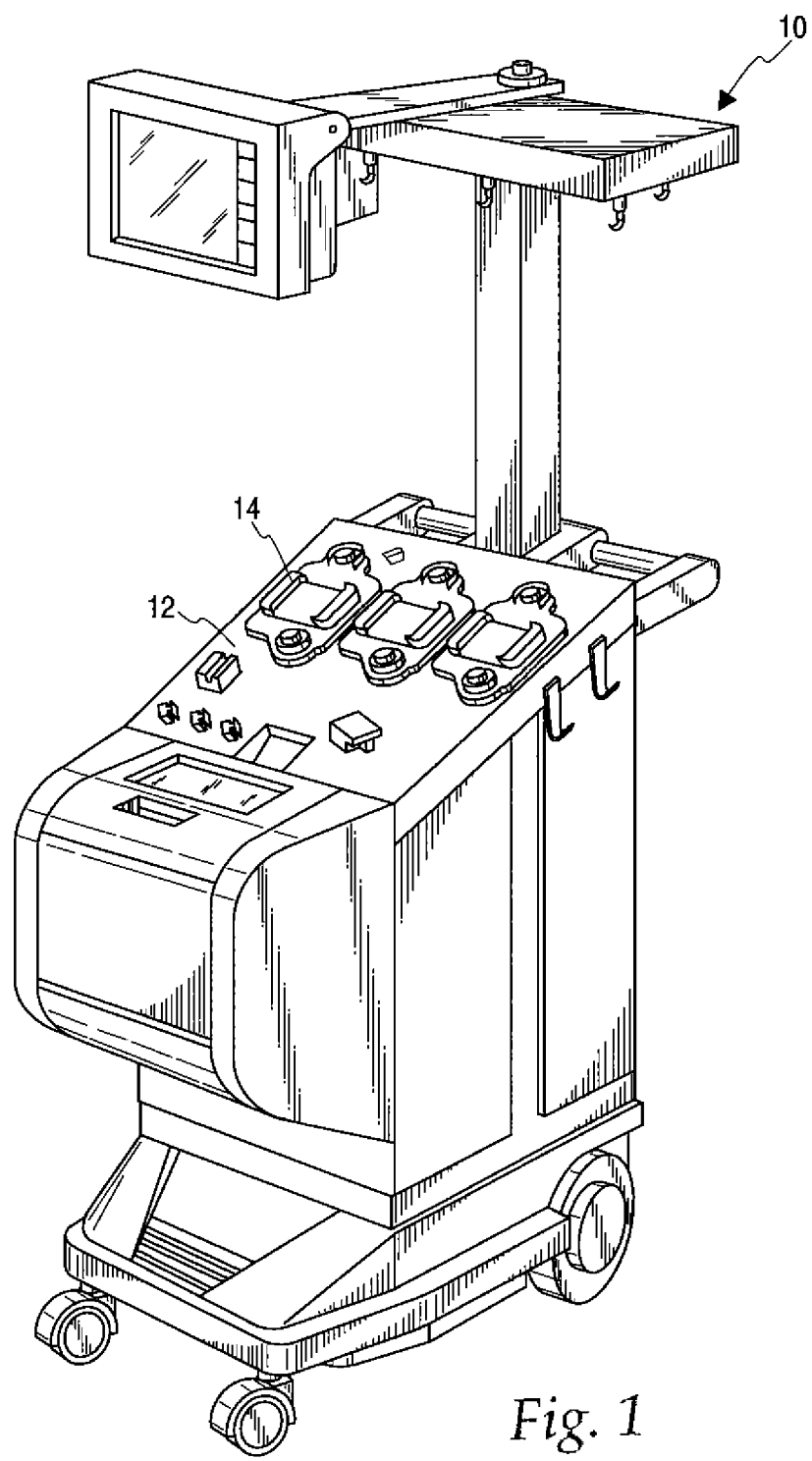
FIG. 1 is a perspective view of an exemplary durable fluid processing centrifuge system that may be used in combination with cassettes and sheeting according to the present disclosure.

FIG. 1 shows a known centrifugal fluid processing system 10 that may be used in combination with cassettes and sheeting according to the present disclosure. The system is currently marketed as the AMICUS® separator by Fenwal, Inc. of Lake Zurich, Ill. The system 10 can be used for processing various fluids, but is particularly well suited for processing whole blood and other suspensions of biological cellular materials. The system 10 includes a centrifuge chamber (not visible) suitable for separating a fluid into its components based on the density of such components. A more detailed description of the centrifuge and the other elements of the system 10 can be found in U.S. Pat. No. 5,868,696, which is incorporated by reference herein. While various aspects of the present invention will be described in the context of their use with the system 10 of FIG. 1, it should be understood that the cassettes and sheeting described herein may be used in other fluid processing applications and with other fluid processing systems such as, but not limited to, dialysis machines.

Figure 2:
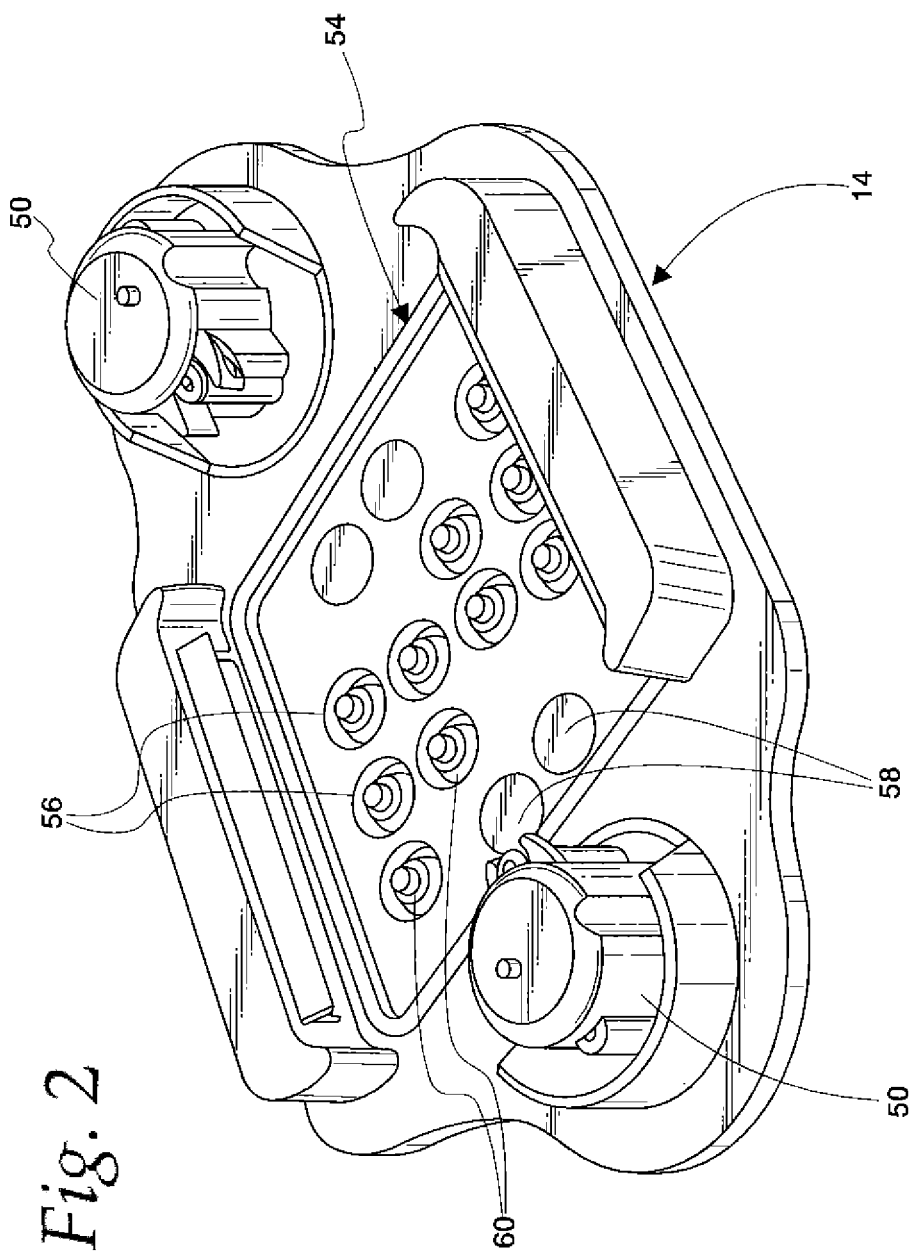
FIG. 2 is a perspective view of a cassette holder of the fluid processing system of FIG. 1.

A sloped front panel 12 of the system 10 includes at least one cassette holder 14, which is shown in greater detail in FIG. 2. The cassette holder 14 is configured to receive and grip a fluid processing cassette 16 (FIGS. 3 and 4) of a disposable, single use processing set. An exemplary processing set that is suitable for use with the system 10 of FIG. 1 can be found in U.S. Pat. No. 5,868,696, although it should be understood that the cassettes and sheeting described herein may also be incorporated into other processing sets without departing from the scope of the present disclosure.

Figure 3:
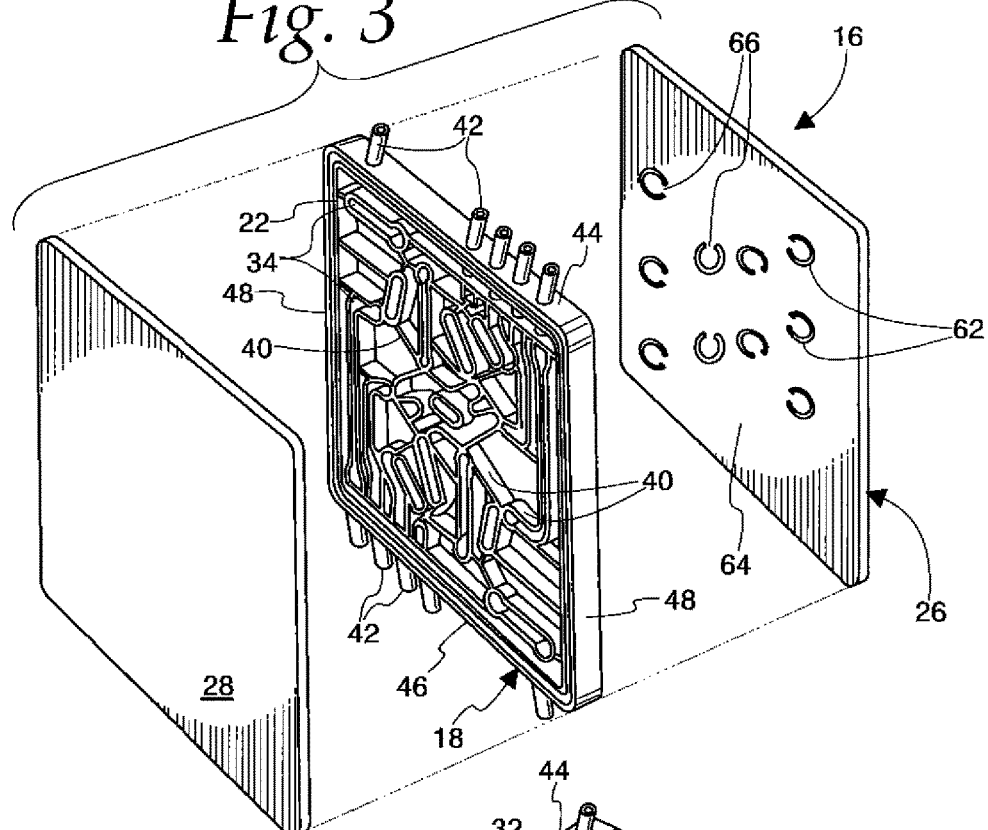
FIG. 3 is an exploded perspective view of a disposable fluid processing cassette that may be used in combination with the fluid processing system of FIG. 1.
Figure 4:
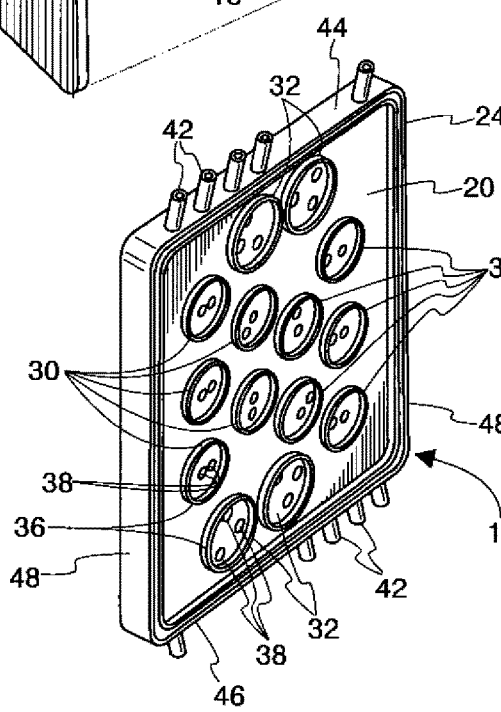
FIG. 4 is a perspective view of an underside of the fluid processing cassette of FIG. 3.

The illustrated cassette 16, as shown in FIGS. 3 and 4, includes an injection-molded body 18 that is compartmentalized by an interior wall 20 (FIG. 4) to present or form a topside 22 (FIG. 3) and an underside 24 (FIG. 4). For the purposes of description, the topside 22 is the side of the cassette 16 that, in use, faces away from the system 10, while the underside 24 faces towards the system 10. A flexible sheeting or diaphragm 26 overlies and peripherally seals the underside 24 of the cassette 16. A generally rigid upper panel 28 overlies the topside 22 of the cassette 16 and is sealed peripherally and to the raised channel-defining walls in the cassette 16, as described later.

In one embodiment, the cassette 16, the interior wall 20, and the upper panel 28 are made of a rigid medical grade plastic material, while the sheeting 26 is made of a flexible sheet of medical grade plastic, such as polyvinyl chloride or silicone. The upper panel 28 and the sheeting 26 are sealed about their peripheries to the peripheral edges of the top- and undersides 22, 24 of the cassette 16, respectively.

As shown in FIGS. 3 and 4, the top- and undersides 22, 24 of the cassette 16 contain preformed cavities. On the underside 24 of the cassette 16 (FIG. 4), the cavities form an array of valve stations 30 and an array of pressure sensing stations 32. On the topside 22 of the cassette 16 (FIG. 3), the cavities form an array of channels or paths 34 for conveying liquids. The valve stations 30 communicate with the liquid paths 34 through the interior wall 20 to interconnect them in a predetermined manner. The sensing stations 32 also communicate with the liquid paths 34 through the interior wall 20 to sense pressures in selected regions. The number and arrangement of the liquid paths 34, the valve stations 30, and the sensing stations 32 can vary. In the illustrated embodiment, the cassette 16 provides nineteen liquid paths 34, ten valve stations 30, and four sensing stations 32.

The valve and sensing stations 30, 32 resemble shallow wells open on the cassette underside 24 (FIG. 4). Upstanding edges 36 rise from the interior wall 20 and peripherally surround the valve and sensing stations 30, 32. The valve stations 30 are closed by the interior wall 20 on the topside 22 of the cassette 16, except that each valve station 30 includes a pair of through holes or fluid flow ports 38 in the interior wall 20. The ports 38 each open into selected different liquid paths 34 on the topside 22 of the cassette 16.

The sensing stations 32 are likewise closed by the interior wall 22 on the topside 22 of the cassette 16, except that each sensing station 32 includes three through holes or ports 38 in the interior wall 20 (FIG. 4). The ports 38 open into selected liquid paths 34 on the topside 22 of the cassette 16. These ports 38 channel liquid flow among the selected liquid paths 34 through the associated sensing station 32.

In one embodiment, the flexible sheeting 26 overlying the underside 24 of the cassette 16 is sealed by ultrasonic welding or other suitable means to the upstanding peripheral edges 36 of the valve and sensing stations 30, 32. This isolates the valve stations 30 and sensing stations 32 from each other and the rest of the system. In an alternative embodiment, the flexible sheeting 26 can be seated against the upstanding edges 36 by an external positive force applied by the cassette holder 14 against the sheeting 26. The positive force, like the ultrasonic weld, peripherally seals the valve and sensing stations 30, 32.

The localized application of additional positive force (referred to herein as a "closing force") upon the intermediate region of the sheeting 26 overlying a valve station 30 serves to flex the sheeting 26 into the valve station 30. Such closing force is provided by the cassette holder 14 or valve members associated therewith, as will be described in greater detail herein. The sheeting 26 seats against one of the ports 38 to seal the port 38, which closes the valve station 30 to liquid flow. Upon removal of the closing force, fluid pressure within the valve station 30 and/or the plastic memory of the sheeting 26 itself helps to unseat the sheeting 26 from the port 38, opening the valve station 30 to liquid flow. Most advantageously, the sheeting 26 is provided with a biasing feature, such as the biasing member 62 (FIGS. 3 and 5), associated with each valve station 30 and configured to further assist in unseating the sheeting 26 from the port 38, as will be described in greater detail.

Upstanding channel sides or edges 40 rise from the interior wall 20 to peripherally surround and define the liquid paths 34, which are open on the topside 22 of the cassette 16. The liquid paths 34 are closed by the interior wall 20 on the underside 24 of the cassette 16, except for the ports 38 of the valve and sensing stations 30, 32 (FIG. 4). The rigid panel 28 overlying the topside 22 of the cassette 16 is preferably, but not exclusively, sealed by ultrasonic welding to the upstanding peripheral edges 40, sealing the liquid paths 34 from each other and the rest of the system.

In the illustrated embodiment, a plurality of (e.g., ten) pre-molded tube connectors 42 extend out along opposite side edges 44, 46 of the cassette 16. The tube connectors 42 are arranged five on one side edge 44 and five on the other side edge 46. The other side edges 48 of the cassette 16, as illustrated, are free of tube connectors. The tube connectors 42 are associated with external tubing (not illustrated) to associate the cassette 16 with the remainder of the disposable set.

The tube connectors 42 communicate with various interior liquid paths 34, which constitute the liquid paths of the cassette 16 through which a fluid enters or exits the cassette 16. The remaining interior liquid paths 34 of the cassette 16 constitute branch paths that link the liquid paths 34 associated with the tube connectors 42 to each other through the valve stations 30 and sensing stations 32.

Turning now to the cassette holder 14 (FIG. 2), it receives and retains or grips the cassette 16 along the two opposed sides edges 48 in the desired operating position. The cassette holder 14 includes a pair of peristaltic pump stations 50. When the cassette 16 is gripped by the cassette holder 14, tubing loops extending from the cassette 16 (defined by selected tube connectors 42) make operative engagement with the pump stations 50. The pump stations 50 are operated to cause fluid flow through the cassette 16.

Figure 7:
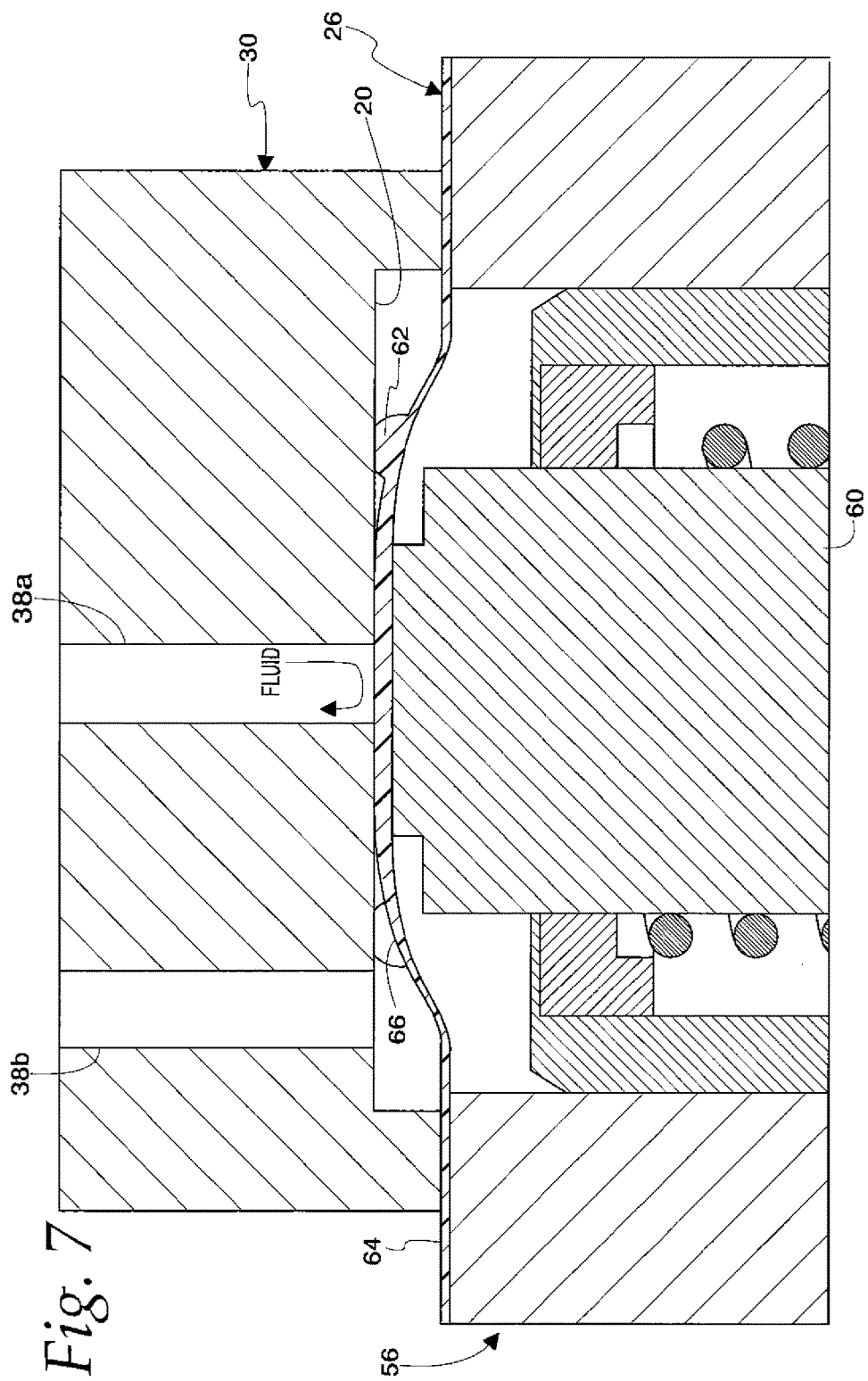
FIG. 7 is a cross-sectional view of the valve station and cassette holder of FIG. 6, with the piston in an extended position.

The flexible sheeting 26 covering the underside 24 of the cassette 16 is urged into intimate contact with a valve and sensor array or assembly 54 by the cassette holder 14 (FIGS. 6 and 7). The valve assembly 54 acts in concert with the valve stations 30 and sensing stations 32 of the cassette 16. The particular illustrated valve assembly 54 illustrated in FIG. 2 includes ten valve actuators 56 and four pressure sensing transducers 58, although the number of such actuators and transducers is not controlling. The valve actuators 56 and the pressure sensing transducers 58 are mutually arranged in the same layout as the valve stations 30 and sensing stations 32 on the underside 24 of the cassette 16. When the cassette 16 is mounted on the cassette holder 14, the valve actuators 56 align with the cassette valve stations 30. At the same time, the pressure sensing transducers 58 mutually align with the cassette sensing stations 32.

The pressure sensing transducers 58 sense liquid pressures in the sensing stations 32 of the cassette 16. The sensed pressures are transmitted to a controller of the system 10 as part of its overall system monitoring function.

As for the valve actuators 56, each includes an electrically actuated solenoid pin or piston 60. Each piston 60 is independently movable between a retracted position (FIG. 6) and an extended position (FIG. 7). When in its extended position, the piston 60 presses against the region of the sheeting 26 that overlies the associated valve station 30. In this position, the piston 60 flexes the sheeting 26 into the associated valve station 30, thereby sealing the associated valve port 38. This closes the valve station 30 to liquid flow. When in its retracted position, the piston 60 does not apply force against the sheeting 26. As before described, the plastic memory of the sheeting 26 and the biasing member 62 biases the sheeting 26 away from the cassette body 18 to unseat the sheeting 26 from the valve port 38, thereby opening the valve station 30 to liquid flow.

FIG. 5 shows a particular embodiment of a biasing member 62. Other embodiments of biasing members according to the present disclosure are illustrated in FIG. 8 (identified as biasing member 62a) and FIG. 9 (identified as biasing member 62b). The various embodiments of the biasing members are shown separately, with a particular sheeting 26 including only one type of biasing member (see FIG. 3). This may be advantageous in terms of obtaining a uniform response from the various biasing members, but it is also within the scope of the present disclosure for a particular sheeting 26 to include differently configured biasing members, which may be advantageous if the needs of the associated valve stations 30 vary.

The sheeting 26 comprises a generally flexible layer 64 (i.e., the diaphragm-like, flexible sheet of material that overlays the underside 24 of the cassette 16), with each biasing member 62-62b being associated with the side facing the cassette body 18. In particular, each biasing member 62-62b is configured to be positioned between the interior wall 20 and the generally flexible layer 64 of the sheeting 26, received within one of the valve stations 30, as shown in FIGS. 6-9. As for the particular location of the biasing members 62-62b within the valve stations 30, it may vary, as will be described in greater detail.

In the embodiment of FIG. 5, the biasing member 62 is oriented to be adjacent to the port 38a that is closed by action of the piston 60 (see FIGS. 6 and 7), which may be referred to herein as the first port. The biasing member 62 does not entirely encircle or surround that port 38a, but only partially or substantially surrounds the port 38a, as best shown in FIG. 5 (with the relative positions of the ports 38a and 38b being shown in broken lines). The biasing member 62 of FIG. 5 includes an opening or passage 66, which is less than the maximum height of the biasing member 66 or (as illustrated in FIG. 5) has a zero height (i.e., only the generally flexible layer 64 of the sheeting 26 is present in the location of the opening 66).

In one embodiment, the biasing member 62 is configured to be in constant contact with the interior wall 20, regardless of whether the piston 60 is in the extended position (FIG. 7)

or the retracted position (FIG. 6). By providing an opening 66, fluid is allowed to pass between the ports 38a and 38b when the piston is in the retracted position (FIG. 6), despite the biasing member 62 contacting the interior wall 20. In the embodiment of FIG. 5, the opening 66 is oriented so as to provide a direct or straight fluid flowpath between the ports 38a and 38b, but the opening 66 may be positioned elsewhere (i.e., at a different angular position) without departing from the scope of the present disclosure. However, it may be advantageous for the opening 66 to present a direct fluid flowpath between the ports 38a and 38b to decrease the length of the flowpath between the ports 38a and 38b.

In the illustrated embodiment, the biasing member 62 is generally concentric with the port 38a and generally arcuate or C-shaped to define the opening 66. The biasing member 62 may define an arc greater than 180° or greater than 300° to substantially, but not entirely, surround the port 38a and define the opening 66. The illustrated configuration is merely exemplary, as the biasing member may have any other (preferably, but not necessarily, non-closed) shape to define an opening 66, an need not be circular or semicircular. It could, for example, be in the general shape of a square, oval, or polygon or other configuration. It may be advantageous for the biasing member 62 to be configured and oriented so as to be spaced away from (i.e., be out of alignment with) the uppermost end or tip of the piston 60. For example, in the embodiment of FIGS. 5-7, the biasing member 62 defines an open interior that is generally the same size as (or slightly larger than) the perimeter of the uppermost end or tip of the piston 60, such that the piston 60 does not directly compress the biasing member 62 when in the extended position of FIG. 7. Additionally, while FIGS. 5-7 show the biasing member 62 as having a generally uniform height, except at and adjacent to the opening 66, it is also within the scope of the present disclosure for the biasing member 62 to have a non-uniform height at locations other than the opening 66.

The biasing member 62 of FIG. 5 may be comprised of the same material as the generally flexible layer 64 (which may be silicone in one embodiment) or a different material. If the biasing member 62 and generally flexible layer 64 are comprised of the same material, the biasing member 62 may comprise a molded protrusion or extension of the generally flexible layer 64, being formed at the same time as the generally flexible layer 64. Alternatively, the biasing member 62 may be separately secured to the generally flexible layer 64 (e.g., by an adhesive or weld or other suitable fixation method), regardless of whether it is made of the same material as the generally flexible layer 64 or a different material.

In other embodiments, the biasing member 62 may be secured to the interior wall 20 of the cassette body 18 (or some other portion of the cassette body 18), rather than being secured to the generally flexible layer 64. It is also within the scope of the present disclosure for the biasing member 62 to be secured to both the generally flexible layer 64 of the sheeting 26 and the cassette body 18 or to neither (e.g., by press-fitting the biasing member 62 into the space between the generally flexible layer 64 and the interior wall 20).

In use, the cassette 16 is loaded onto the valve assembly 54, with the generally flexible layer 64 of the sheeting 26 in engagement with the valve actuators 56 (optionally with a membrane or cover of the valve assembly 54 positioned above the valve actuators 56) and the valve stations 30 aligned with the valve actuators 56. The pistons 60 of the valve actuators 56 are in the retracted position of FIG. 6 when the cassette 16 is loaded onto the valve assembly 54. With the piston 60 in the retracted position, fluid is free to flow between the ports 38a and 38b. In one embodiment, fluid flows from port 38a, through the opening 66 defined by the biasing member 62, and into the port 38b to continue passing through the cassette 16, as shown in FIG. 6. In other embodiments, fluid flow may be reversed, with the fluid moving from the second port 38b to the first port 38a via the opening 66 of the biasing member 62.

When it becomes desirable to prevent flow through the valve station 30, the piston 60 is actuated to move from the retracted position to the extended position of FIG. 7. In the extended position, the piston 60 presses the generally flexible layer 64 of the sheeting 26 against the interior wall 20 of the cassette 16 so as to cover the port 38a, thereby preventing fluid flow through the valve station 30. The biasing member 62 resists movement of the sheeting 26 toward the interior wall 20, but is sufficiently compliant to allow the piston 60 to fully seat the generally flexible layer 64 against the interior wall 20. Although not necessarily directly compressed by the piston 60, the biasing member 62 is deformed and compressed when the piston 60 is in the extended position, as shown in FIG. 7.

When it becomes desirable to again allow flow through the valve station 30, the piston 60 is actuated to move from the extended position of FIG. 7 to the retracted position of FIG. 6. Due to a fluid flow-created vacuum within the cassette 16, the tendency of the sheeting 26 to return to its initial, non-stressed configuration of FIG. 6 may not be sufficient to fully unseat the generally flexible layer 64 from the port 38a. Compared to the generally flexible layer 64, the biasing member 62 has a greater resiliency or capacity to return to its initial configuration of FIG. 6. Accordingly, removing the force of the piston 60 from the sheeting 26 allows the biasing member 62 to return to its initial configuration and, in so doing, also unseats the generally flexible layer 64 from the port 38a and returns the sheeting 26 to its initial configuration.

In an alternative embodiment, shown in FIG. 8, the biasing member 62a is oriented to be adjacent to the port 38a that is closed by action of the piston 60, similar to the embodiment of FIG. 5. However, rather than surrounding only a portion of the port 38a, the biasing member 62a of FIG. 8 may entirely encircle or surround that port 38a. Even if the biasing member 62a is configured to be in constant contact with the cassette interior wall 20 (including when the piston 60 is in the retracted position of FIG. 6), fluid may flow through the biasing member 62a, between the ports 38a and 38b. This may be achieved in any of a number of ways. In the embodiment illustrated in FIG. 8, the biasing member 62a comprises a spring, such as a wave spring or a coil spring, which has open areas between adjacent coils to allow fluid flow therethrough. If provided as a wave or coil spring, the biasing member 62a may be comprised of any of a number of materials, including a metallic material or a polymeric material. In other embodiments, the biasing member may have a generally open or porous structure, such as a foam insert or ring, to allow fluid flow therethrough. Other configurations of a biasing member that allows fluid flow therethrough may also be employed without departing from the scope of the present disclosure.

In the illustrated embodiment, the biasing member 62a is generally concentric with the port 38a, with an inner diameter slightly larger than the perimeter of the uppermost end or tip of the piston 60, such that the piston 60 does not directly compress the biasing member 62a when in an extended position. However, it is also within the scope of the present disclosure for the biasing member 62a to be non-concentric with the port 38a and/or to have an inner diameter less than or equal to the perimeter of the uppermost end or tip of the piston 60. Further, the biasing member 62a may be either substantially annular or non-annular without departing from the scope of the present disclosure.

FIG. 8 shows the interior wall 20 of the cassette 16 modified to include a groove or channel or recess 68 that receives one of the ends of the biasing member 62a. The recess 68 may include an adhesive or other means to fixedly secure the biasing member 62a therein. In other embodiments, one end of the biasing member 62 is press-fit into the recess 68 to secure it to the interior wall 20. In other embodiments, the biasing member may be configured to fit loosely into the recess 68, such that the biasing member 62a is held in place with respect to the associated port 38a. The opposite end of the biasing member 62a may be secured to or separate from the generally flexible layer 64 of the sheeting 26. It is also within the scope of the present disclosure to omit the recess 68 and secure the biasing member 62a directly to the cassette interior wall 20 and/or the generally flexible layer 64 of the sheeting 26.

In use, the biasing member 62a of FIG. 8 operates similarly to the biasing member 62 of FIGS. 5-7. When the cassette 16 has been loaded onto the valve assembly 54, the pistons 60 of the valve actuators 56 are in the retracted position of FIG. 8 to allow fluid flow through the biasing members 62a, between the respective ports 38a and 38b. When it becomes desirable to prevent flow through the valve station 30, the piston 60 is actuated to move from the retracted position to the extended position, in which the piston 60 presses the generally flexible layer 64 of the sheeting 26 against the interior wall 20 of the cassette 16 so as to cover the port 38a, thereby preventing fluid flow through the valve station 30. The biasing member 62a resists movement of the sheeting 26 toward the interior wall 20, but is sufficiently compliant to allow the piston 60 to fully seat the generally flexible layer 64 against the interior wall 20. Although not necessarily directly compressed by the piston 60, the biasing member 62a is deformed and compressed when the piston 60 is in the extended position.

When it becomes desirable to again allow flow through the valve station 30, the piston 60 is actuated to move back to the retracted position of FIG. 8. The tendency of the biasing member 62a to return from its compressed condition (when the piston 60 is extended) to its relaxed or initial condition (FIG. 8) assists in unseating the generally flexible layer 64 from the port 38a and returning the sheeting 26 to its initial configuration.

In another alternative embodiment, shown in FIG. 9, the biasing member 62b is oriented to be adjacent to the port 38a that is closed by action of the piston 60, similar to the embodiments of FIGS. 5 and 8. However, rather than surrounding all or a portion of the port 38a, the biasing member 62b of FIG. 9 is configured independently of the port 38a (i.e., it is not shaped to encircle the port 38a or follow its contours). It will be appreciated that the biasing members 62 and 62a may be repositioned and/or reconfigured so as to be independent of the port 38a, and such biasing members 62 and 62a are not limited to a shape and orientation that are reliant upon the shape and/or location of the associated port 38a.

In the illustrated embodiment, the biasing member 62b is positioned opposite the second port 38b (i.e., 180° away from the second port 38a when viewed with respect to the first port 38a). This location helps to prevent the biasing member 62b from interfering with fluid flow between the ports 38a and 38b. However, it is within the scope of the present disclosure for the biasing member 62b to be positioned at other locations, including between the two ports 38a and 38b, which allows for fluid communication between the ports 38a and 38b through and/or around the biasing member 62b (depending on its configuration). Most advantageously, the biasing member 62b is positioned adjacent to the perimeter of the uppermost end or tip of the piston 60, which provides a strong spring response without compromising the functionality of the piston 60. However, it is also within the scope of the present disclosure for the biasing member 62b to be positioned elsewhere within the valve station 30, including locations farther from the piston 60 and the port 38a.

The biasing member 62b of FIG. 9 may be comprised of any of a number of materials. For example, it may be comprised of the same material as the generally flexible layer 64 (as in the embodiment of FIG. 5) or a metallic or polymeric or foam material (as in the embodiment of FIG. 8). In the illustrated embodiment, the biasing member 62b comprises an elastomeric spacer or insert. Additionally, there may be more than one biasing member 62b positioned within a particular valve station 30, and the various biasing members within a particular valve station 30 may be differently configured. For example, a particular valve station 30 could be provided with one biasing member comprising a spacer or insert of elastomeric material and another biasing member comprising a metallic flat spring. The biasing member 62b may be secured to the generally flexible layer 64 and/or the interior wall 20 by any suitable means or it may be secured to neither surface.

The biasing member 62b of FIG. 9 operates similarly to the biasing members 62 and 62a of FIGS. 5-8, being compressed when the piston 60 moves into an extended position, and then returning to its initial configuration when the piston 60 moves back to the retracted position so as to assist in unseating the generally flexible layer 64 from the port 38a and returning the sheeting 26 to its initial configuration.

Besides the biasing members illustrated herein, other configurations may also be employed without departing from the scope of the present disclosure. For example, the biasing member may be configured to completely or partially surround both ports 38a and 38b or only the second port 38b (i.e., the port that is not directly valved by the piston 60). Also, the biasing member does not necessarily have to be in constant contact with the cassette interior wall 20, but may be spaced away from the interior wall 20 when the piston 60 is in the retracted position and only in contact with the interior wall 20 when the piston 60 is in the extended position or an intermediate position between the extended and retracted positions.

Additionally, while the biasing members illustrated and described herein are relatively resilient (i.e., having the tendency to deform upon an applied force from the piston 60 and then return to their initial configuration), non-resilient configurations may also be employed. For example, the biasing member may comprise a rigid, substantially non-deformable projection from the cassette body 18, preferably positioned adjacent to the first port 38a and extending toward the sheeting 26. Such a projection may be integrally formed with the cassette body 18 or formed separately and subsequently secured to the cassette body 18. Alternatively, the projection may be secured to the sheeting 26 instead of the cassette body 18. The projection is configured so as to allow the sheeting 26 to be pressed over the first port 38a, while resisting the movement of the sheeting 26 toward the cassette body 18. Thus, the mere presence of the substantially rigid projection, rather than any inherent resiliency, assists in biasing the sheeting 26 away from the closed position and toward the open position.

Aspects of the present subject matter described above may be beneficial alone or in combination with one or more other aspects. Without limiting the foregoing description, in accordance with one aspect of the subject matter herein, there is provided a sheeting for use with a fluid processing cassette having at least one valve station with a plurality of fluid flow ports. The sheeting comprises a generally flexible layer and a biasing member. The sheeting has first and second sides, with the biasing member being associated with one of the sides of the generally flexible layer and configured to be received within the valve station of the cassette.

In accordance with another aspect which may be used or combined with the preceding aspect, the biasing member is comprised of the same material as the generally flexible layer.

In accordance with another aspect which may be used or combined with any of the preceding aspects, the biasing member comprises a molded protrusion of the generally flexible layer.

In accordance with another aspect which may be used or combined with any of the preceding aspects, the biasing member is generally arcuate.

In accordance with another aspect which may be used or combined with any of the preceding aspects, the biasing member is generally C-shaped.

In accordance with another aspect which may be used or combined with the first aspect, the biasing member comprises a spring.

In accordance with another aspect which may be used or combined with the first aspect, the biasing member comprises a foam insert.

In accordance with another aspect, there is provided a fluid processing cassette, which includes an interior wall defining a topside and an underside. At least one valve station is associated with the underside of the interior wall. A plurality of fluid flow ports are associated with one of the valve stations. The cassette also includes a sheeting comprising a generally flexible layer having first and second sides. A biasing member is associated with one of the sides of the generally flexible layer and positioned between the interior wall and the generally flexible layer, within the valve station.

In accordance with another aspect which may be used or combined with the preceding aspect, the biasing member is comprised of the same material as the generally flexible layer.

In accordance with another aspect which may be used or combined with any of the preceding two aspects, the biasing member comprises a molded protrusion of the generally flexible layer.

In accordance with another aspect which may be used or combined with any of the preceding three aspects, the biasing member is generally arcuate.

In accordance with another aspect which may be used or combined with any of the preceding four aspects, the biasing member is generally C-shaped.

In accordance with another aspect which may be used or combined with the eighth aspect, the biasing member comprises a spring.

In accordance with another aspect which may be used or combined with the eighth aspect, the biasing member comprises a foam insert.

In accordance with another aspect which may be used or combined with any of the preceding seven aspects, the biasing member engages the interior wall and the generally flexible layer.

In accordance with another aspect which may be used or combined with any of the preceding eight aspects, the interior wall includes a channel receiving one end of the biasing member.

In accordance with another aspect which may be used or combined with any of the preceding nine aspects, the biasing member partially surrounds one of the fluid flow ports.

In accordance with another aspect which may be used or combined with the eighth aspect, the biasing member surrounds one of the fluid flow ports.

In accordance with another aspect, there is provided the combination of a fluid processing system and a disposable processing set. The combination includes a fluid processing cassette and a valve actuator. The fluid processing cassette includes an interior wall, at least one valve station, and a plurality of fluid flow ports, and a sheeting. The interior wall defines a topside and an underside, with the at least one valve station being associated with the underside of the interior wall. A plurality of fluid flow ports are associated with one of the valve stations. The sheeting includes a generally flexible layer having first and second sides and a biasing member associated with one of the sides. The biasing member is positioned between the interior wall and the generally flexible layer, within the valve station.

In accordance with another aspect which may be used or combined with the preceding aspect, the biasing member is comprised of the same material as the generally flexible layer.

In accordance with another aspect which may be used or combined with any of the preceding two aspects, the biasing member comprises a molded protrusion of the generally flexible layer.

In accordance with another aspect which may be used or combined with any of the preceding three aspects, the biasing member is generally arcuate.

In accordance with another aspect which may be used or combined with any of the preceding four aspects, the biasing member is generally C-shaped.

In accordance with another aspect which may be used or combined with the nineteenth aspect, the biasing member comprises a spring.

In accordance with another aspect which may be used or combined with the nineteenth aspect, the biasing member comprises a foam insert.

In accordance with another aspect which may be used or combined with any of the preceding seven aspects, the biasing member engages the interior wall and the generally flexible layer when the piston is in the extended and retracted positions.

In accordance with another aspect which may be used or combined with any of the preceding eight aspects, the interior wall includes a channel receiving one end of the biasing member.

In accordance with another aspect which may be used or combined with any of the preceding nine aspects, the biasing member partially surrounds one of the fluid flow ports.

In accordance with another aspect which may be used or combined with the nineteenth aspect, the biasing member surrounds one of the fluid flow ports.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the sheeting alone, the sheeting in combination with the hardware or cassette, and/or the sheeting in combination with the hardware and cassette.

The invention claimed is:

1. A fluid processing cassette comprising:
   an interior wall defining a topside and an underside;
   at least one valve station associated with the underside of the interior wall;
   first and second fluid flow ports each comprising a through hole in the interior wall within said at least one valve station, wherein the at least one valve station comprises an upstanding edge surrounding the first and second fluid flow ports; and
   a sheeting overlying the underside of the interior wall, sealed or seated to the upstanding edge of the at least one valve station, and comprising
      a generally flexible layer having first and second sides and an intermediate region overlaying the at least one valve station and configured so that, upon localized application of a closing force upon the intermediate region, the generally flexible layer flexes into the at least one valve station and into contact with the underside of the interior wall within said at least one valve station to seat against the first fluid flow port to seal the first fluid flow port, which closes the at least one valve station for fluid flow, and
      a biasing member associated with one of the sides of the generally flexible layer, positioned between the underside of the interior wall and the generally flexible layer, within the at least one valve station, and biased to unseat the generally flexible layer from the first fluid flow port by directly contacting the underside of the interior wall within said at least one valve station.

2. The fluid processing cassette of claim 1, wherein the biasing member is comprised of the same material as the generally flexible layer.

3. The fluid processing cassette of claim 1, wherein the biasing member comprises a generally arcuate protrusion of the generally flexible layer.

4. The fluid processing cassette of claim 1, wherein the biasing member is generally C-shaped.

5. The fluid processing cassette of claim 1, wherein the biasing member comprises a spring.

6. The fluid processing cassette of claim 1, wherein the biasing member comprises a foam insert.

7. The fluid processing cassette of claim 1, wherein the biasing member partially surrounds one of the first and second fluid flow ports.

8. The fluid processing cassette of claim 1, wherein the biasing member surrounds one of the first and second fluid flow ports.

9. The fluid processing cassette of claim 1, wherein the biasing member is configured to be deformed and compressed upon the localized application of the closing force.

10. A fluid processing system and a disposable processing set combination comprising:
    a fluid processing cassette including
       an interior wall defining a topside and an underside,
       at least one valve station associated with the underside of the interior wall,
       first and second fluid flow ports each comprising a through hole in the interior wall within said at least one valve station, wherein the at least one valve station comprises an upstanding edge surrounding the first and second fluid flow ports, and
       a sheeting overlying the underside of the interior wall, sealed or seated to the upstanding edge of the at least one valve station, and comprising
          a generally flexible layer having first and second sides and an intermediate region overlaying the at least one valve station and movable into contact with the underside of the interior wall within said at least one valve station to seat against the first fluid flow port to seal the first fluid flow port, and
          a biasing member associated with one of the sides of the generally flexible layer, positioned between the underside of the interior wall and the generally flexible layer, within the at least one valve station, and biased to unseat the generally flexible layer from the first fluid flow port by directly contacting the underside of the interior wall within said at least one valve station; and
    a valve actuator configured to engage the sheeting of the cassette and including a piston substantially aligned with the first fluid flow port when the sheeting of the cassette is in engagement with the valve actuator, wherein
       the piston is configured to move between an extended position, in which the piston applies localized application of a closing force upon the intermediate region to flex the generally flexible layer of the sheeting into the at least one valve station and into contact with the interior wall of the cassette within the at least one valve station so as to cover the first fluid flow port and thereby prevent fluid flow through the at least one valve station, and a retracted position, in which the piston is spaced away from the cassette so as to allow the generally flexible layer of the sheeting to uncover the first fluid flow port and thereby allow fluid flow through the at least one valve station, and
       the biasing member is configured to assist in displacing the generally flexible layer of the sheeting from the first fluid flow port when the piston moves from the extended position to the retracted position.

11. The combination of claim 10, wherein the biasing member is comprised of the same material as the generally flexible layer.

12. The combination of claim 10, wherein the biasing member comprises a generally arcuate protrusion of the generally flexible layer.

13. The combination of claim 10, wherein the biasing member comprises a spring.

14. The combination of claim 10, wherein the biasing member comprises a foam insert.

15. The combination of claim 10, wherein the biasing member partially surrounds one of the first and second fluid flow ports.

16. The combination of claim 10, wherein the biasing member surrounds one of the first and second fluid flow ports.

* * * * *